United States Patent
Konig et al.

(10) Patent No.: US 9,072,589 B2
(45) Date of Patent: Jul. 7, 2015

(54) ASSEMBLY AND METHOD FOR PERFORMING SURGICAL LASER TREATMENTS OF THE EYE

(71) Applicant: WaveLight AG, Erlangen (DE)

(72) Inventors: Karsten Konig, Saarbrucken (DE); Ronan Le Harzic, Sarreguemines (FR); Christian Wullner, Mohrendorf (DE); Christof Donitzky, Eckental (DE)

(73) Assignee: Wavelight GmbH, Erlangen (DE)

( * ) Notice: Subject to any disclaimer, the term of this patent is extended or adjusted under 35 U.S.C. 154(b) by 0 days.

(21) Appl. No.: 13/731,689

(22) Filed: Dec. 31, 2012

(65) Prior Publication Data

US 2013/0158529 A1    Jun. 20, 2013

Related U.S. Application Data

(63) Continuation-in-part of application No. 12/093,580, filed as application No. PCT/EP2006/010968 on Nov. 15, 2006, now Pat. No. 8,343,142.

(30) Foreign Application Priority Data

Nov. 17, 2005    (EP) ..................................... 05025133

(51) Int. Cl.
   *A61F 9/008*    (2006.01)

(52) U.S. Cl.
   CPC ............... *A61F 9/008* (2013.01); *A61F 9/0084* (2013.01); *A61F 2009/00872* (2013.01)

(58) Field of Classification Search
   CPC ............... A61F 9/008; A61F 9/00084; A61F 2009/00872; A61F 9/00836
   USPC ....................................... 606/2–6; 607/88, 89
   See application file for complete search history.

(56) References Cited

U.S. PATENT DOCUMENTS

| | | |
|---|---|---|
| 5,656,186 A | 8/1997 | Mourou et al. |
| 5,984,916 A | 11/1999 | Lai |
| RE37,504 E | 1/2002 | Lin |
| 7,131,968 B2 * | 11/2006 | Bendett et al. .................. 606/10 |
| 2004/0199149 A1 | 10/2004 | Myers et al. |
| 2005/0085800 A1 | 4/2005 | Lenzer et al. |
| 2006/0100613 A1 * | 5/2006 | McArdle et al. .................. 606/4 |

FOREIGN PATENT DOCUMENTS

EP    1537841 A2    6/2005

OTHER PUBLICATIONS

Written Opinion of the International Searching Authority issued for PCT/EP2006/010968, Nov. 15, 2006, 7 pgs.
Korean Office Action with English Translation issued for Korean Application No. 7011673/2008 dated Jan. 15, 2013, 10 pgs.

* cited by examiner

*Primary Examiner* — Darryl J Collins
(74) *Attorney, Agent, or Firm* — Haynes and Boone, LLP

(57) ABSTRACT

An arrangement for carrying out surgical laser treatments of the eye is adapted to emit pulsed treatment radiation with a wavelength of between about 190 nm and about 380 nm and a pulse duration in the femtosecond range. Such treatment radiation allows nonaggressive corneal or intraocular laser treatment of the eye, for example in order to make corneal cuts or deliberately ablate corneal tissue.

13 Claims, 1 Drawing Sheet

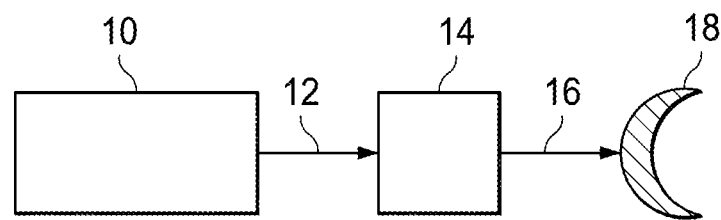

ASSEMBLY AND METHOD FOR PERFORMING SURGICAL LASER TREATMENTS OF THE EYE

CROSS-REFERENCE TO RELATED APPLICATIONS

This application is a continuation-in-part of U.S. patent application Ser. No. 12/093,580, filed Jun. 15, 2009, which is a United States national phase application of international patent application number PCT/EP2006/010968, filed Nov. 15, 2006, which claims priority of European Application No. 05025133.9 filed Nov. 17, 2005, each of which is hereby incorporated by reference in its entirety.

BACKGROUND

The invention relates to an arrangement and a method for carrying out surgical laser treatments of the eye.

It is known in the prior art to use so-called femtosecond lasers, i.e. pulsed lasers with pulse durations in the femtosecond range, for ophthalmological surgery, particularly in order to separate tissue structures on or in the eye. For example, femtosecond lasers are used to perform so-called flap cuts, i.e. incisions into the eye from the side in order to produce a small flap which is folded to the side, for example for a LASIK intervention. Femtosecond lasers are also employed in so-called keratoplasty.

Femtosecond lasers previously used in ophthalmological surgery have generally emitted radiation with wavelengths in the IR range or in the visible range of the electromagnetic spectrum.

U.S. Pat. No. 5,984,916 relates to corneal and intraocular laser surgery, employing pulsed laser radiation whose pulse duration lies between 10 fs and 2 ps with a wavelength of about 400 nm upwards.

U.S. Pat. No. 5,656,186 describes a method for determining a suitable pulse duration for processing a very wide variety of materials with pulsed laser radiation. According to this method, the dependency of the threshold for optical penetration of the material on the pulse duration is initially determined experimentally for a given wavelength. In a curve describing the dependency which is found, a point is then determined from which, towards shorter pulse durations, a quadratic dependency of the penetration threshold on the pulse duration no longer applies. The laser processing per se is then carried out with a pulse duration on the other side of this transition point. Pulse durations in the femtosecond and picosecond range are indicated for this.

The method described in U.S. Pat. No. 5,656,186 is intended to be applicable in an extremely wide wavelength range, which covers virtually the entire laser spectrum used in practice. In any event, a wavelength range of from 200 nm to 2 μm is mentioned in this document. As examples of the variety of materials for which the method is intended to be applicable, metals such as gold and aluminium, glass materials but also living tissue are mentioned, in particular the cornea. For laser treatment of the cornea, a wavelength of 770 nm is specifically indicated.

SUMMARY

It is an object of the invention to provide an arrangement and a method for carrying out surgical laser treatments of the eye, with which improved operation results are achievable. In particular, the arrangement and the method should allow undesired modifications in the tissue structures of the eye to be avoided better, for example damage to the lens or the retina during interventions in the cornea.

The invention is based on the discovery that by the action of pulsed treatment radiation with a wavelength of between about 190 nm and about 380 nm and a pulse duration in the femtosecond range, undesired impairments of eye regions which are not intended to be affected by the electromagnetic radiation during the operation can be avoided better.

When using radiation in the infrared range or in the visible range, however, such damage cannot (always) be ruled out.

The arrangement according to the invention preferably comprises means for focusing the treatment radiation on or in a cornea. It is thereby possible to surgically intervene only on the cornea, in particular by a photoablation and/or photodisruption, for instance in order to ablate superficial or intratissue corneal material and/or make cuts in the cornea, for example in order to produce a corneal flap in the scope of a LASIK treatment. It is thus possible to avoid significantly affecting other structures of the eye, for example the lens and/or the retina.

BRIEF DESCRIPTION OF THE DRAWING

FIG. 1 is a schematic illustration of a laser treatment system arrangement in accordance with the present disclosure.

DETAILED DESCRIPTION

According to a preferred configuration of the invention, the wavelength of the emitted treatment radiation lies between about 190 nm and about 200 nm or between about 260 nm and about 280 nm or between about 340 nm and about 360 nm. In particular, the wavelength of the emitted treatment radiation may be about 193 nm or about 267 nm or about 345 nm or about 347 nm. The 347 nm wavelength may be generated for example by frequency tripling from a basic wavelength of 1040 nm. The wavelength 193 nm may for example be generated from a basic wavelength of 1064 nm. In some instances, the basic wavelength is between about 1020 nm and about 1080 nm, with some embodiments having a basic wavelength between about 1030 nm and about 1035 nm. The person skilled in the art is familiar with frequency conversion concepts, for which reason details of the frequency conversion need not be discussed in detail here. Suitable converters may be constructed for example with components such as optical parametric generators/oscillators, sum-frequency generators and generators for the second, third, fourth or fifth harmonic. Femtosecond lasers which emit the two aforementioned basic wavelengths, as well as other wavelengths in the near infrared range, are readily available commercially. The wavelength 267 nm may for example be generated as a third harmonic of the emission wavelength of a Ti:Sa laser.

It has been found that when using laser pulses with the said wavelengths and pulse durations in the femtosecond range for corneal treatment, for instance in order to produce a flap, virtually all of the incident radiation is converted in the cornea, and any radiation passing through the cornea as residual transmission is absorbed by the human lens and not in the retina.

As a result of relatively high pulse repetition rates, is also possible to reduce the so-called ablation threshold beyond which—statistically speaking—photoablation takes place to a significant extent. At least for a wavelength of the emitted treatment radiation between about 340 nm and about 360 nm, a pulse repetition rate for the treatment radiation is therefore preferably at least about 10 kHz in the invention, preferably between about 100 kHz and about 500 kHz. A pulse repetition rate into the MHz range may of course also be selected, even for example in the two-digit or three-digit MHz range. In some instances, the repetition rate is between about 100 kHz and about 100 MHz. In one particular embodiment, the repetition rate is about 1 MHz.

At least for a wavelength of the emitted treatment radiation between about 340 nm and about 360 nm, the pulse energy for the treatment radiation is preferably between about 0.1 nJ and about 5 μJ in the invention, preferably at most about 10 nJ. For example, pulse energies of not more than 0.8 nJ per pulse may be set, in particular not more than 0.7 nJ per pulse and more particularly not more than 0.5 nJ per pulse. The minimum energy limit values depend in this case on the repetition rate and the numerical aperture, and they are respectively to be adjusted so that the desired effect takes place, i.e. for example the ablation threshold is reached. In some instances, the pulse energy is between about 1.0 nJ and about 500 nJ.

As an example, the invention makes it possible to produce a corneal flap of the highest quality for the LASIK operation using pulsed UV radiation with only 0.5 nJ/pulse. A time of from 30 seconds to 1 minute for producing in the flap is thereby achievable.

The term femtosecond range in the scope of the invention is also intended to include pulse lengths of several hundred fs, i.e. for example pulse lengths with an FWHM length of 230 fs. In particular, this term is also intended to include pulse lengths in the single-digit picosecond range up to about 10 ps. For example, the pulse lengths with FS lasers may be stretched to 1 ps by using suitable optical means. In some implementations, the pulse lengths are between the picosecond range and the attosecond range, including the femtosecond range. In that regard, unless otherwise specifically noted, each range of pulse lengths is understood to include all values from 0.1 to 1,000 for the relevant time period such that, for example, the attosecond range includes values from 0.1 attoseconds to 1,000 attoseconds (i.e., 1.0 femtosecond) and the femtosecond range includes values from 0.1 femtoseconds to 1000 femtoseconds (i.e., 1.0 picosecond). In some instances, the pulse length is between about 500 attoseconds and about 10 picoseconds.

An exemplary embodiment of the invention will be described below with reference to the single appended FIGURE. The FIGURE schematically shows a laser treatment system with a pulsed femtosecond laser 10.

The laser 10 delivers a wavelength of 347 nm by generating the third harmonic from a basic wavelength of 1040 nm. The emitted radiation pulses 12 have pulse lengths of 250 fs (FWHM) with a repetition rate of 20 MHz. The power is 27 mW. Beam shaping and guiding means are indicated overall by the block 14, and are known per se to the person skilled in the art. These means are adapted in particular to steer the radiation pulses so that the entire target region is covered. The means 14 are also equipped with a focusing function which makes it possible to focus the radiation pulses onto a desired point, which may for example lie on the surface of the target tissue or in its depth. The radiation pulses which are thus controlled in time and space by the means 14, and which are now denoted by 16, are directed in the represented exemplary case onto a cornea 18, for instance in order to produce a flap.

If so desired, the beam shaping and guiding means may also contain an objective lens arrangement. This, however, is not compulsory in the scope of the invention.

Good ablation results may for example be achieved by a wavelength of 347 nm with repetition rates in the range of 20 MHz, a maximum energy of 1 nJ per pulse and by using a UV focusing objective (100×). This corresponds approximately to a fluence of 2 $J/cm^2$. In other instances, the fluence of the treatment radiation is between 0.3 $J/cm^2$ and about 0.5 $J/cm^2$.

With the aforementioned parameters, virtually complete radiation absorption is possible in the cornea together with extremely small radiation penetration into other eye regions. High-quality flaps can be produced in an acceptable time of less than 1 minute with a very low pulse energy.

What is claimed is:

1. An arrangement for carrying out surgical laser treatments of the eye, the arrangement comprising:
    a laser source configured to emit pulsed treatment radiation with a wavelength between about 340 nm and about 360 nm and a pulse duration in a range between an attosecond range and a picosecond range, wherein the emitted pulsed treatment radiation wavelength is generated from a basic wavelength of between about 1020 nm and about 1084, wherein the wavelength of the emitted pulsed treatment radiation is generated as a third harmonic of the basic wavelength and wherein a pulse repetition rate of the emitted pulsed treatment radiation is between about 100 kHz and about 100 MHz;
    wherein the wavelength of the emitted pulsed treatment radiation is between about 340 nm and about 350 nm; and
    wherein the basic wavelength is about 1040 nm.

2. The arrangement of claim 1, further comprising a focusing objective in optical communication with the laser source, the focusing objective configured to focus the emitted pulsed treatment radiation onto a cornea of the eye.

3. The arrangement of claim 1, wherein a pulse energy of the emitted pulsed treatment radiation is between about 1.0 nJ and about 500 nJ.

4. The arrangement of claim 1, wherein the emitted pulsed treatment radiation has a fluence between about 0.3 $J/cm^2$ and about 0.5 $J/cm^2$.

5. A method for carrying out a surgical laser treatment of an eye, the method comprising:
    emitting pulsed treatment radiation with a wavelength between about 340 nm and about 360 nm and a pulse duration in a range between an attosecond range and a picosecond range, wherein the emitted pulsed treatment radiation wavelength is generated from a basic wavelength of between about 1020 nm and about 1084 nm, wherein the wavelength of the emitted pulsed treatment radiation is generated as a third harmonic of the basic wavelength and wherein a pulse repetition rate of the emitted pulsed treatment radiation between about 100 kHz and about 100 MHz;
    wherein the wavelength of the emitted pulsed treatment radiation is between about 340 nm and about 350 nm; and
    wherein the basic wavelength is about 1040 nm.

6. The method of claim 5, further comprising focusing the emitted pulsed treatment radiation onto a cornea of the eye to produce a corneal flap for a LASIK procedure.

7. The method of claim 6, wherein the corneal flap is produced in less than about 1 minute.

8. The method of claim 5, wherein a pulse energy of the emitted pulsed treatment radiation is between about 1.0 nJ and about 500 nJ.

9. The method of claim 5, wherein the emitted pulsed treatment radiation has a fluence between about 0.3 $J/cm^2$ and about 0.5 $J/cm^2$.

10. A system for laser treatment of the eye, the system comprising:
    a laser source adapted to emit a radiation having a basic wavelength between about 1020 nm and about 1084 nm;

a frequency converter for converting the radiation to a treatment pulse with a wavelength between about 340 nm and about 360 nm, wherein the wavelength of the treatment pulse is a third harmonic of the basic wavelength; and a controller for controlling the treatment pulse to a duration in a range from about 1 picosecond to about 1 attosecond and for controlling a pulse repetition rate of the treatment pulse to be about 100 kHz and about 100 MHz;

wherein the wavelength of the emitted treatment pulse radiation is between about 340 nm and about 350 nm;

wherein the basic wavelength is about 1400 nm.

11. The system of claim 10, further comprising a focusing objective in optical communication with the laser source, the focusing objective configured to focus the pulsed treatment pulse radiation onto a cornea of the eye.

12. The system of claim 10, wherein a pulse energy of the treatment pulse radiation is between about 1.0 nJ and about 500 nJ.

13. The system of claim 10, wherein the treatment pulse radiation has a fluence between about 0.3 J/cm$^2$ and about 0.5 J/cm$^2$.

* * * * *